United States Patent [19]

Rosenberg

[11] 4,013,558
[45] Mar. 22, 1977

[54] SYSTEM FOR PURIFYING LIQUIDS

[76] Inventor: H. Colman Rosenberg, 1921 NE. 185th Terrace, North Miami Beach, Fla. 33161

[22] Filed: Mar. 18, 1975

[21] Appl. No.: 559,427

Related U.S. Application Data

[63] Continuation-in-part of Ser. No. 443,416, Feb. 19, 1974, abandoned, and Ser. No. 255,646, May 22, 1972, abandoned.

[52] U.S. Cl. .................................. 210/149; 210/152; 210/233; 210/243; 210/342; 210/444
[51] Int. Cl.² .......................... C02B 3/06; C02C 5/06
[58] Field of Search ......... 21/54 R, 102 R, DIG. 2; 210/1–4, 12, 64, 71, 104, 142, 149, 150, 151, 152, 195 R, 197, 243, 233, 234, 235, 337, 338, 342, 444; 315/39.53

[56] References Cited
UNITED STATES PATENTS

| | | | |
|---|---|---|---|
| 2,630,919 | 3/1953 | Tyler | 210/233 |
| 2,851,164 | 9/1958 | Morino | 210/342 X |
| 3,152,077 | 10/1974 | Kryzer | 210/233 |
| 3,170,868 | 2/1965 | Atkinson | 210/149 X |
| 3,494,723 | 2/1970 | Gray | 21/54 R |
| 3,523,076 | 8/1970 | Goerz, Jr. et al. | 210/64 X |
| 3,535,234 | 10/1970 | Gilwood | 210/12 X |
| 3,537,655 | 11/1970 | Gustafson | 210/152 X |
| 3,607,737 | 9/1971 | Gamer | 210/149 X |
| 3,617,539 | 11/1971 | Grutsch et al. | 210/195 X |
| 3,753,651 | 8/1973 | Boucher | 21/54 R |
| 3,788,472 | 1/1974 | Boschen et al. | 210/149 X |
| 3,854,875 | 12/1974 | Bosshardt | 210/64 X |

Primary Examiner—Charles N. Hart
Assistant Examiner—Robert H. Spitzer

[57] ABSTRACT

An improved method for treating liquids by disinfection and clarification which includes a means to mix and maintain consistency of the flow in a generally uniform composition prior to and during treatment. The mixture being connected to a section of conduit arranged in a pattern in a target area of a microwave generator so that all matter in the flow is exposed and excited by the electro-magnetic energy for a predetermined period of time and a control means to regulate flow of the mixture so as to allow flow only when mixture is treated, to a prescribed level. The method includes an automatic means to sense degree of treatment and to increase or decrease flow, as required, to maintain uniformity of treatment. Disposable filter means is provided when removal of undesirable contaminents is required.

5 Claims, 7 Drawing Figures

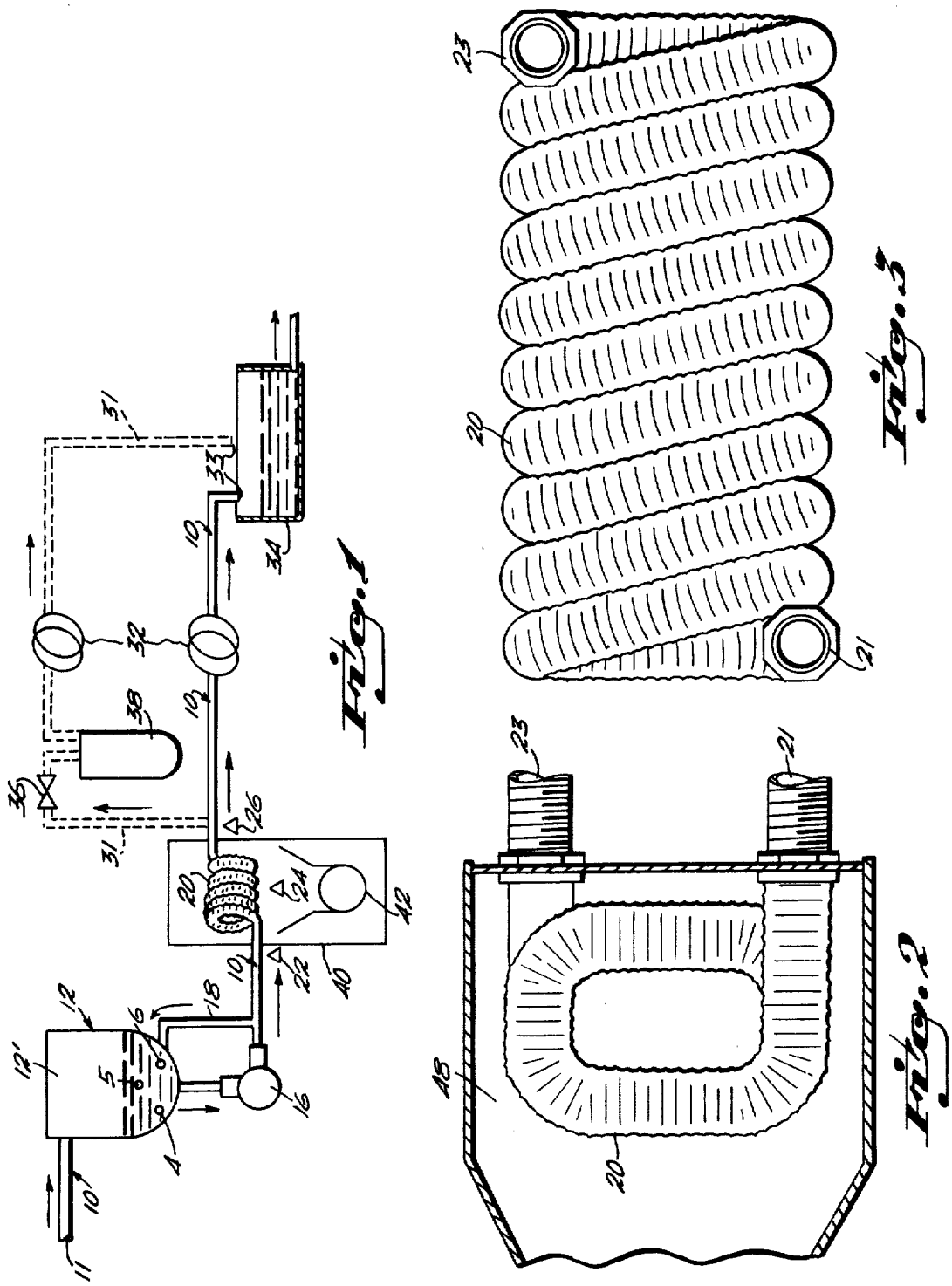

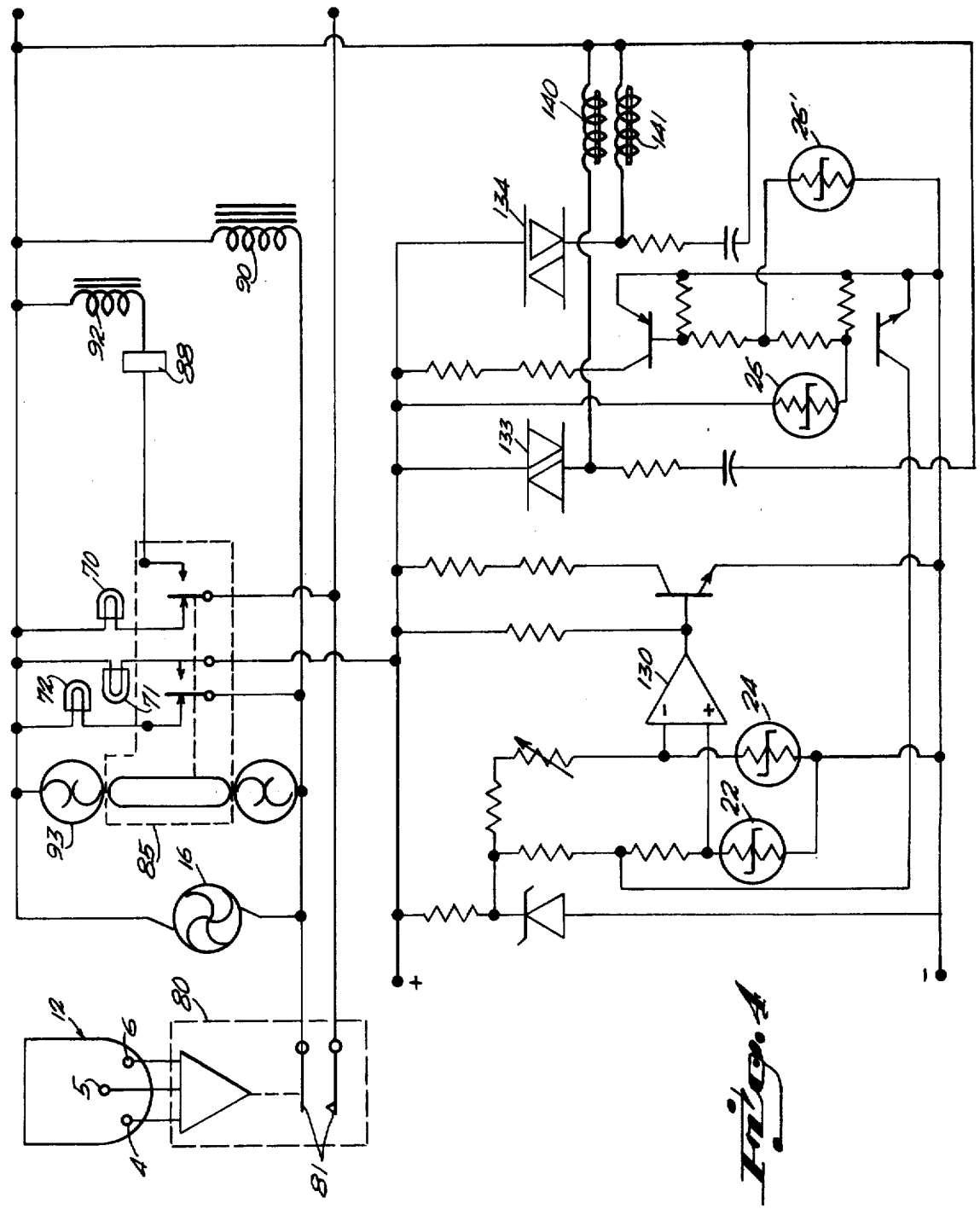

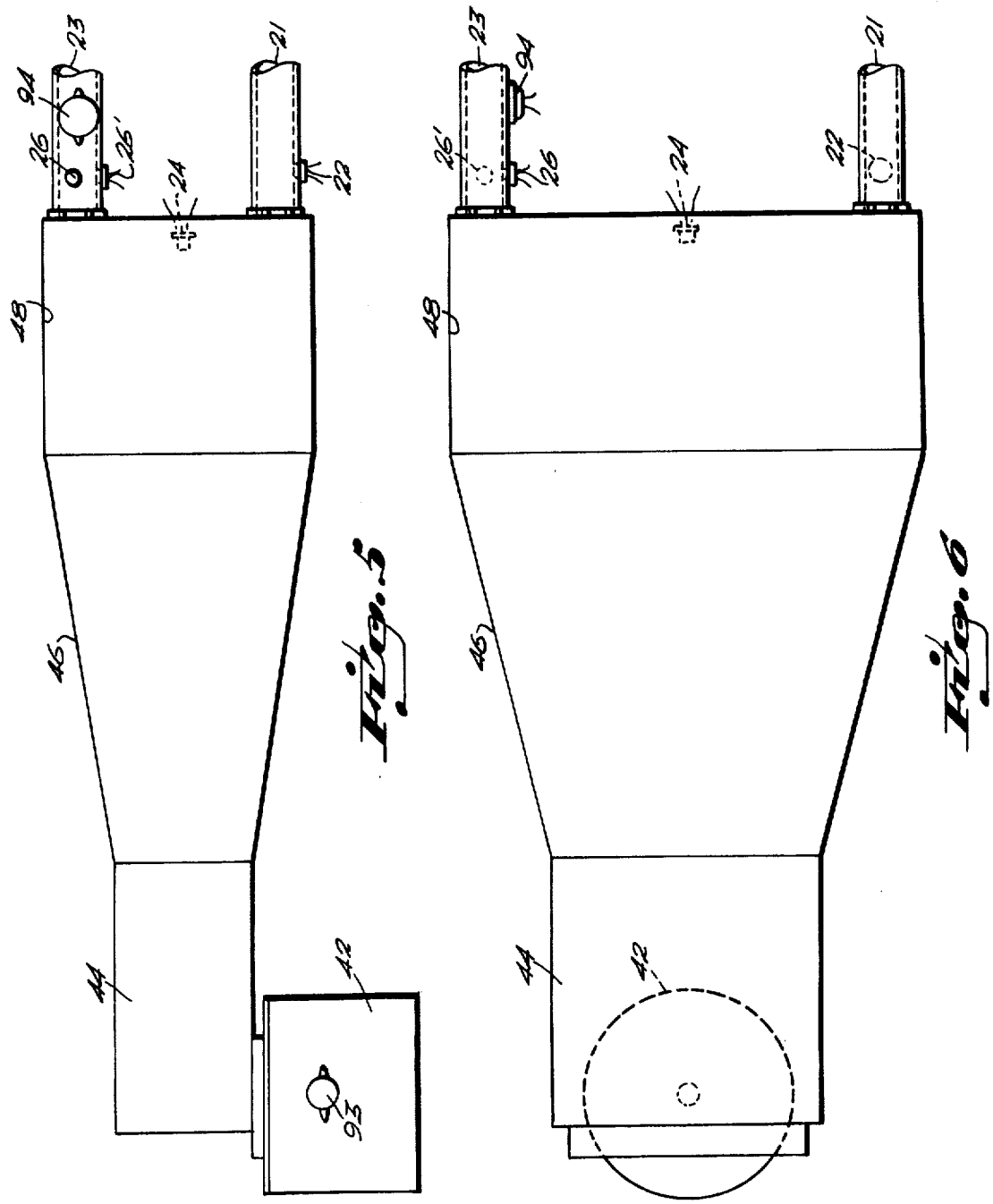

SYSTEM FOR PURIFYING LIQUIDS

This case is a continuation-in-part of U.S. patent application Ser. No. 443,416 filed Feb. 19, 1974 and Ser. No. 255,646 filed May 22, 1972, both abandoned.

BACKGROUND OF THE INVENTION

The need for purification of liquids such as water, wastewater, processed foods, pharmaceuticals and industrial coolants is well known. In the past, most disinfection was by thermal or chemical means and in the case of water and wastewater, the principal disinfector has been chlorine. However, chlorine in most of its forms is highly reactive, poisonous and caustic. More recently, chlorine has been linked to cancer-producing agents in drinking water.

Thermal disinfection also is limited to material which can be heated to boiling temperatures or higher and maintained at those temperatures for prolonged periods. Some spore forming bacteria will survive temperatures of 123° C for periods in excess of 30 minutes.

Some liquids cannot be treated with chemical disinfectants nor can they be subjected to prolonged boiling temperatures without destroying some essential characteristics. These include certain pharmaceuticals, some processed foods and many industrial coolants.

In purification, there is often a need to clarify or separate out various foreign matter. In wastewater treatment, special flocculants or coagulating agents such as alum are added to improve the separation of solid matter, the general practice being to treat the solids separately and in most cases, the solids are disposed of without disinfection.

In treatment of water and wastewater, Biochemical Oxygen Demand (BOD) or Oxygen Demand (OD) is a criteria of water purity. Chemical disinfection increases the BOD necessitating aeration to improve the dissolved oxygen content of the water and to oxidize the disinfectant. Then additives, such as calcium carbonate, are utilized to counteract the taste and odor of the disinfectant in drinking water. These additives need to be removed prior to use adding another step to the purification process.

Purification of liquids entails the use of energy in one form or another and the level of liquid purity is usually directly related to the energy input.

In the past, treatment of materials by microwave irradiation has been suggested; however, because of complexities; such as lack of homogenity, variations in electrical characteristics of each material and the energy containment and emission problem; practical microwave systems have not heretofore been developed.

Water, the most extensive and allotropic of all known solvents, may contain solids, gases and/or other liquids altering the dielectric constant, electrical conductivity and resultant microwave absorption. Therefore, a constant monitoring and control is necessary during treatment to assure purification and maximum energy efficiency.

SUMMARY OF THE INVENTION

This invention relates to the treatment of liquids or semi-liquids such as water, wastewater, oils, foods, pharmaceuticals, and any other material with a liquid component, which can be made to flow through a conduit. Inherent in this invention are improved methods for handling the material during the treatment cycle and controlling the flow in order to improve the efficiency ratio of energy input versus level of treatment. It includes a purifier which treats the material by exposing it to microwave radiation while maintaining the material in a complex flow pattern such that the radiated energy is caused to impinge on all of the material during the treatment. This is accomplished by a device designated, an Inspirator, which creates a rotational fluid flow during the exposure cycle. Furthermore, the level of treatment is constantly sensed and rate of flow increased or decreased accordingly to maintain prescribed treatment for the type of material under treatment.

Many liquid purification requirements include separation of contaminents from the liquid. This is particularly true with waste effluents which may have suspended solids, colloidal matter and other dissolved material. It is accordingly another object of this invention, to provide an improved separation method so designed as to capture the contaminents in an easily removable container.

It is a general object of this invention to provide an improved fluid treatment device, which is adaptable to a wide range of applications. This device is particularly appropriate for transportable utilization since it is relatively small and light, can be used to process small amounts of liquids on an intermittent cycle; can be secured for long periods without effecting its processing capability; or can be used in a continuous round-the-clock mode.

Furthermore, the inherent versatility of the instant invention provides for a wide range of sizes. Units have been made to operate efficiently at flow rates from a few quarts per hour, to several gallons per hour. Tests indicate an increase in energy efficiency can be effected with larger purifiers which can process fluids at thousands of gallons per hour. Additionally, effectivity of the microwave purification increases as the level of contamination or the ionic nature of the liquid increases.

In accordance with these and other objects which will be apparent in view of the following description, the Instant Invention is deemed to possess new and useful art.

DESCRIPTION OF THE INVENTION

The instant invention will be described with reference to the accompanying drawings in which:

FIG. 1 is a flow diagram of the instant invention;

FIG. 2 is a side elevation of the microwave waveguide cavity showing the Inspirator placement;

FIG. 3 is an illustration of the Inspirator designated by the numeral 20 in FIGS. 1 and 2.

FIG. 4 is a simplified electrical diagram of the instant invention illustrating the control means for the purifier and flow controls.

FIGS. 5 and 6 are side and top views of the waveguide showing input and output ports and placement of control sensors.

Figure 7:
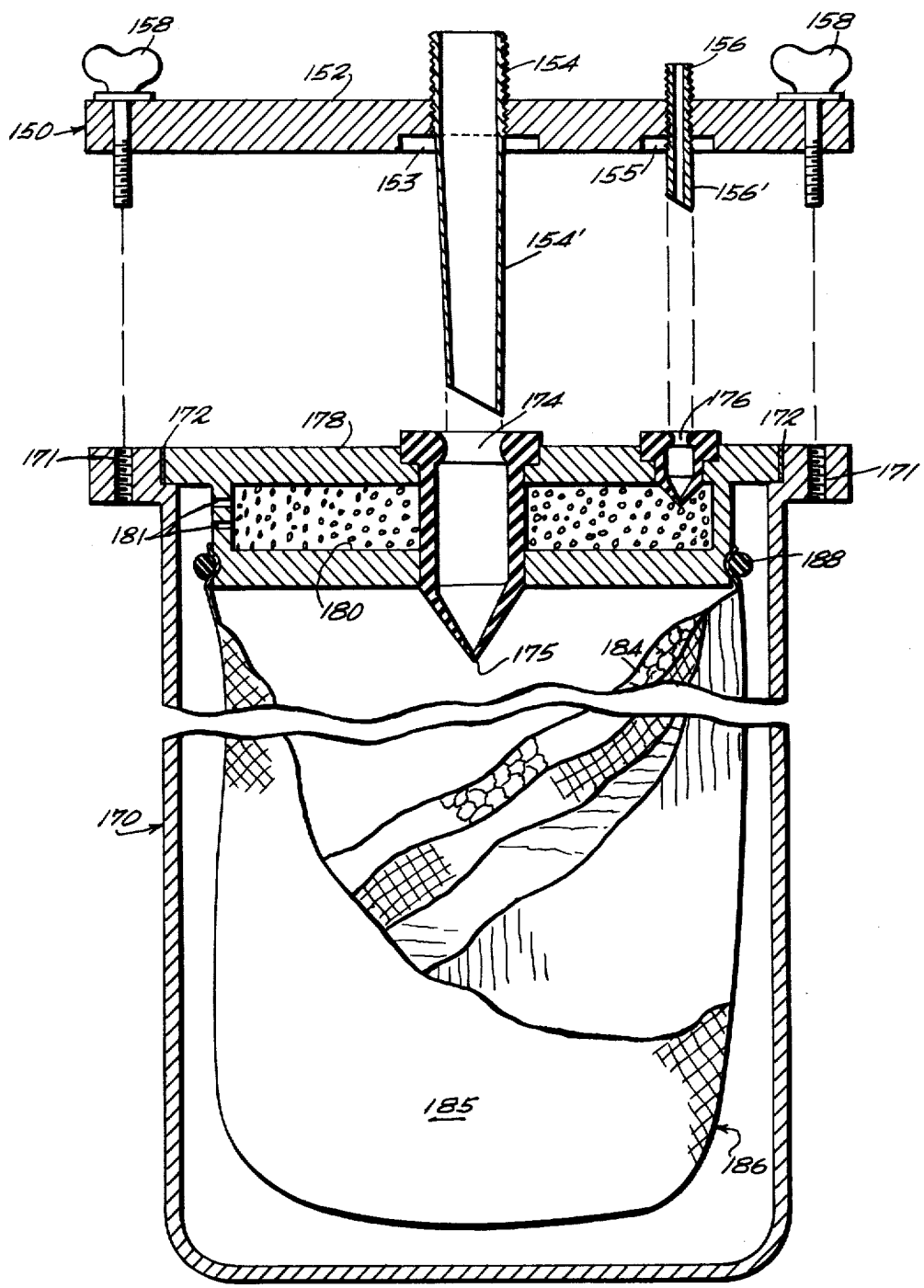
FIG. 7 is an illustration of the filter design showing improved disposable features.

Referring to the drawings wherein like reference characters designate like or corresponding parts throughout the several views, there is shown in FIG. 1, a representative system or device and an alternate system to be used when clarification of liquids is a requirement. The system includes a line for fluid flow which is generally designated by the numberal 10 and in which there is an input 11, a pretreatment storage and mixing means 12 and thereafter in downstream relation, a disinfecting means 40, the output of which is controlled by control means 32 and thence to a main outlet 33 which may discharge into a storage tank 34. As an alternate when clarification of the fluids is required, a filter means 38 is inserted in the line downstream of the purifier means 40 and upstream of the control means 32. Furthermore, a shutoff valve 36 is provided, between the purifier means 40 and the filter means 38, to prevent fluid leakage or flow when the filter means 38 is opened for disposal.

In a typical sterilization installation, the upstream inlet of the line 10 directs inflowing liquids from a source into a pretreatment tank 12 wherein are located liquid level sensors 4, 5, and 6 which activate the purification cycle when the liquid rises to a predetermined level.

With continued reference to FIG. 1, it is seen that pump 16 which is in series with the tank 12 causes mixing as will be explained. The pump provides a pressure head which causes a component of the fluid to flow to the purifier device 40 to be described; and in the preferred embodiment, the agitation means includes a recirculation line 18 which directs the major component of the outflow of pump 16 through line 18 into the lower part of tank 12, the flowpath for the recycled material preferably leading tangentially into the tank chamber 12' to cause a rotational or turbulent mixing action within the pretreatment tank 12 which constantly stirs up the tank bottom so that any settleable solids are maintained mixed with the liquid.

Referring to the mixing means, it shall be noted that pump 16 is required to provide a pressure head for fluid flow through the purifier 40 during periods of little or no flow. The normal tendency of centrifugal pumps to cavitate and lose pressure head due to high back pressures, is eliminated by the recycling action, improving overall pump efficiency.

Referring now to the purifier device designated by the numeral 40 in FIG. 1 and shown in more detail in FIGS. 2, 3, 5 and 6, it is seen that it includes a waveguide section 44 extending from a microwave generator 42 toward a target area contained in a closed cavity 48, the waveguide section including an outward diverging or flared section 46. The microwave generator 42 may be a magnetron or other generator of microwave energy designed to emit electromagnetic energy into a waveguide in a transverse electric mode. The frequency range of 2.425 to 2.475 $GH_z$ has been established as a good choice. The microwave energy is directed toward a device in the cavity 48 referred to as an inspirator and designated by the numeral 20 in FIGS. 1, 2, and 3. The cavity 48 is a closed chamber measuring in terms of wavelength, approximately 1½ by ¾ by ¾ at 2.45 $GH_z$ matched to the waveguide 44 by the flared section 46. The design is such that maximum energy is directed toward and absorbed by the fluids within the inspirator 20. Furthermore, any standing waves and reflected energy will have a reinforcing effect on the energy utilization within the inspirator 20 by being absorbed on the return path.

The inspirator 20 in a preferred embodiment is in effect a continuation of the fluid flow line and enclosed in a chamber and occupying 18 centimeters (7 inches) in overall coil length, the uncoiled length measuring approximately 2.4 meters (96 inches) which increases the traverse time for the fluids flowing through the microwave target area by a factor in excess of 10:1.

In the preferred embodiment, the Inspirator 20 is made of fluorocarbons of fluoroplastics commonly known as FEP or TFE. This material was selected for improved performance and characteristics necessary for this application including: low dielectric constant and resultant reduced energy losses; ability to withstand acids, alkalies and organic solvents; non-wetting properties which provide a non-sticking, nonscaling surface; and the ability to retain form under wide variations in temperature.

As is commonly known, liquids flowing in a conduit of consistent cross sectional dimensions, will assume a laminar flow in which the separate laminae may flow at different velocity and inner laminae will retain the central portion of the conduit. The laminar flow tends to separate various constituents of a heterogenious mixture. In order to overcome the laminar flow and to retain a consistent mixture, the inspirator 20 is fabricated of convoluted tubing which is further formed into a coil as is shown in FIGS. 2 and 3. The convolutions alter the inner dimensions of the conduit in a spiral or screw thread fashion; therefore, liquid flow within the device assumes a rotational or tubulent pattern. This action improves the performance of the coil by maintaining a mixing action; providing a longer exposure or transit time; and imparting a self cleaning or wiping action on the inner walls. The result is a device which prevents buildup of inner scale, while assuring a more consistent exposure of all matter flowing through the target area. The coil or inspirator 20 is further improved by flattening the vertical dimension, as shown in FIG. 2, so as to present a broader more uniform frontal area for better absorption of the radiated transverse wave front. Metal fittings, preferably stainless steel, are affixed to the coil ends for connection to the cavity and to provide input 21 and output 23 ports to the purifier.

In performance testing of the instant invention, the exposure time required for sterilization was proven to vary considerably depending on the ionic nature of the fluid being treated. As an example, sea water required only about 60% of the exposure time for disinfection, as did fresh water. The level of solid content also presents variation in exposure time requirement. The testing further indicated that temperature rise was an indicator of reaction to the radiated energy and that sterilization was effected when the reaction to radiation elevated the temperature from ambient or 21° to 65° C. Heat resistant spores were sterilized when exposure elevated the temperature up to between 70° and 80° C; however, temperatures of 100° C or above were no more effective than the lesser thermal levels and only served to decrease system efficiency, wasting energy. Therefore, included in the preferred embodiment, is a means of controlling the degree of treatment by sensing temperature rise and adjusting flow rates so as to retain treatment fidelity. This control means shall be described by reference to FIGS. 1, 4, 5 and 6, wherein like reference characters designate like or corresponding parts throughout the various illustrations.

FIG. 1 shows the location of sensors 22, 24 and 26 and flow control 32 in the flow path; FIGS. 5 and 6 indicate physical placement of sensors 22, 24, 26 and 26' within the purifier; and FIG. 4 shows the electronic relationship of the control means with and to the overall electrical functions.

Fluids entering tank 12 assume a level within same wherein are located electrodes 4, 5 and 6 which are connected to an electronic level control 80. Electrodes 4 and 6 are placed at low liquid level and electrode 5 at the turn-on level. When liquid makes contact with all three electrodes 4, 5 and 6, control 80 is activated closing contacts 81 which turn-on pump 16 starting the mixing action as previously described. Contacts 81 will remain closed until liquid level falls below the low point of the point at which liquid no longer makes contact with electrodes 4 and 6. Contact 81 also initiates a time delay relay 85 and applies power to primary transformer 90 allowing warm-up of microwave generator. When time delay relay 85 times-out, power is applied to microwave generator secondary transformer 92 through relay 88 and power is also applied to the flow control means. The time delay relay 85 also serves to avoid excessive on-off cycling caused by liquid splashing within tank 12, as would be experienced on a ship, boat or land vehicle. A bimetal thermal protector 93 shown in FIG. 5 removes power if generator overheats and thermal protector 94 placed as shown in FIGS. 5 and 6 removes power if liquid exceeds preestablished temperature.

Referring now to lower section of FIG. 1 showing improved control means, temperature sensors 22, 24 26 and 26' operate so as to allow liquid flow only when purifier is activated and liquid is being treated. These sensors are solid state devices commonly known as transition metal polyconductors with a very low thermal time constant in which small changes in temperature create large changes in conductivity within a specific temperature range. As shown in FIGS. 5 and 6, sensor 22 is located in the input port 21 of purifier 40, sensor 24 is placed within the cavity 48 and sensors 26 and 26' are located in purifier output port 23. Amplifier 130 samples ambient temperature sensed by sensor 22 comparing it with temperature sensed by sensor 24. Amplifier 130 is biased to change state when a preestablished differential is attained between 22 and 24, turning on triac 133 and activating solenoid 140, in turn opening a valve with a preset orifice allowing liquid to flow at an initial rate. Liquid flowing through output port 23 is sensed by sensors 26 and 26'. Sensor 26 will change state when optimum treatment is attained in turn activating triac 134 and turning off triac 133 with the effect of inactivating solenoid 140 and activating solenoid 141 which operates a valve with a larger orifice thereby increasing liquid flow. In the event that the second flow level is insufficient, the temperature continues to rise changing the state of sensor 26' which reactivates triac 133 re-energizing solenoid 140 and opening the initial valve again increasing the flow rate. Changes in fluids flowing through the purifier 40 are then constantly sensed and solenoids 140 and 141 will energize and deenergize, depending on temperature levels, modulating the flow rate to maintain continuous treatment at the prescribed level. Although tests have shown that the double solenoid valve providing three flow rates to be adequate, the addition of a third solenoid valve has been used increasing the span of control to as many as seven flow rates.

Referring again to the flow control means shown in FIG. 4, a preferred embodiment utilizes a dual solenoid valve with adjustable orifices. The orifice of valve operated by solenoid 141 is set to allow optimum treatment for the type of material being processed. The orifice of valve operated by solenoid 140 is set at approximately 50% of solenoid 141. The effect is an initial flow on activation of solenoid 140 which is below optimum; therefore, sensor 26 will change state, closing valve 140 and opening valve 141, this should be the normal operating state of the system. Changes in any factor affecting treatment will automatically be accommodated by the 50% above and below normal flow and flow averaging. Major changes in fluid consistency which vary treatment beyond limits of the normal and ± 50% are accommodated by thermostat 93 shown in FIG. 5. Thermostat 93 is normally closed and is placed on output port 23 of purifier 40. When effluent attains the temperature of 90° C, thermostat 93 will open removing power from time delay relay 85 in turn removing power from the microwave generator. The action of thermostat 93 is principally as protection against clogging of the system downstream of purifier 40 and may be used to activate an alarm. This function is especially beneficial when a filter means 38 is included downstream of purifier 40 as shown in dotted path of FIG. 1.

Many fluid or liquid purification requirements include clarification and removal of suspended and dissolved organic and inorganic matter. Filter means are well known and have been used in many forms. However, the instant invention has many varied applications including transportable functions on boats, ships, trains, aircraft, trailers, campers, motor homes and the like. When used for treatment of water and wastewater, filter means must be employed. In some applications, existing known filter means have been used; however, adequate non-leaking disposable filters for use in transportable applications of wastewater treatment were not found. Therefore, in a further embodiment of the instant invention an improved sanitary disposable filter has been included.

Referring to FIG. 7 an improved disposable filter is illustrated. The filter consists of a head generally designated by the numeral 150 and a cannister designated by the numeral 170. The head 150 consists of a circular disc 152 with an input tube 154 at the center and an output tube 156 placed off center. Tubes 154 and 156 are short lengths of conduit threaded on the upper end to attach into disc 152 and to accept input and output fittings, and with a slight taper at 154' and 156'. Thumbscrews 158 are mounted inside the outer periphery of head 150 for attachment of cannister 170. The cannister 170 is an elongated circular container with ears 171 threaded to accept thumbscrews 158 of head 150. Within cannister 170 is a circular insert member 178 with a ledge to fit snugly within cannister 170 and sealed with appropriate cement around points 172 making a solid bond between cannister 170 and insert 178. Projecting down into cannister 170, insert 178 includes a cavity 180 whose outside dimension is approximately 2 centimeters less than the inner dimension of cannister 170. The half section of cavity 180 farthest from output port 176 has small perforations 181 to allow liquid flow. Attached to the lower section of insert 178 at 188 is a filter bag 185 comprised of multiple layers of a well known nylon material, such as is used for ladies hosiery and designated by numeral 184. The multiple nylon bag 184 is contained in a second bag 186 composed of a coarse expandable mesh such as fishing net. Placed in the center of insert 178 is an improved seal and closure means 174 fabricated of flexible material, such as rubber or vinyl, with a tapered pinched end 175 as shown in FIG. 7. The upper section of closure 174 is formed with an internally projecting rounded surface much as an O ring. A second closure and seal 176 is mounted in insert 178 projecting into inner cavity 180. Closure seals 174 and 176 are aligned to accept insertion of input and output tubes 154 and 156 and when cannister 170 is mounted on head 150, tapered ends of tubes 154' and 156' enter closure seals 174 and 176 extending lower pinched ends 175 which form tightly around tubing 154 and 156. As thumbscrews 158 are tightened into tapped holes 171 of cannister 170, closure seals 174 and 176 are drawn into recessed areas 153 and 155 compressing closure seals snuggly around tubing 154 and 156 and against head 150 forming pressure tight seals. When thumbscrews 158 are released and filter cannister 170 is removed, lower end of closure seals 174 and 176 return to closed position preventing leakage of fluids. An additional advantage attributable to closure seals 174 and 176, during use of filter, is reduction of separation pressure against head 150 by confining injected pressures against relatively small surface areas rather than larger diameter of filter head 150.

Referring again to FIg. 7, it will be noted that filtering is accomplished in several stages. The first stage of filtration is through filter bag 185. Fluid is injected into the inner section of filter bag 185 via input conduit 154. Filter bag 185 assumes a relaxed flacid posture when empty, with the fabric fibers forming a fine filter medium. As the bag captures solids, the accumulation forms on the inner walls expanding the bag outward. With the buildup of solid matter on the inner walls and distention of the fabric, the filtration effect tends to remain constant. As filter bag 185 fills the coarse outer netting applies a retentive pressure increasing the ratio of solids to liquids retained. When filter bag 185 bulges against inner surface of cannister 170, the coarse netting of outer bag 186 prevents a hydraulic seal from being formed between the two surfaces and allows filter bag 185 to assume the relative shape of cannister 170. This action provides an improvement in the filter loading factor or the ratio of solids captured versus cubic area in the order of 2:1. Liquids flow from the center of bag 185 through to the outer region and thence upward and into perforations 181 of cavity 180. Cavity 180 is charged with a low porosity filter medium which may be any of the well known carbon granules, diatomaceous earth or like material chosen for the specific filtration requirement. This filter medium is encased in a medium porosity membrane for containment. Combinations of filter mediums to remove phosphates, chlorides and other dissolved matter further extends effectivity of the preferred embodiment.

The instant invention has combined several improvements in treatment of liquids reducing energy consumption, assuring treatment fidelity and reducing sludge handling. The significance to the improvements taught by the instant invention will be appreciated by those skilled in water treatment, for they include:

a. Sterilization in excess of 99.9% for bacteria including typhus, staph, strep, salmonella, botulism without chemical means.

b. Byproduct to the sterilization are deionization and denaturation effects causing precipitation of protien elements and viruses.

c. Reduction of colloidal effects, resulting in improvement in sedimentation of suspended solids by a factor in excess of 2:1 without use of flocculating agents.

d. Improved separation of phosphates, detergents and other dissolved pollutants.

e. An increase in the level of dissolved oxygen despite an increase in temperature.

f. A total system for sterilization and clarification which simultaneously disinfects both liquids and solids and separates the solids into a container for simplified disposal.

What is claimed is:

1. A treatment system for flowable materials composed of liquids and solids which includes:
   A. a line for the flow, said line having an upstream with a main inlet and a downstream with a main outlet;
   B. mixing means in the line to maintain a relatively uniform consistency of the materials; and
   C. purifying means arranged downstream of said mixing means and including a microwave generator, and guide means to direct electromagnetic energy in a path toward a target area of said purifying means,
   D. said line including a pattern in the target area to conduct flow of the flowable material, said pattern comprising a coil which is convoluted to define a whirling or turbulent flow pattern of the flowable material to impart a mixing and wiping action within said coil for even excitation of the flowable material by the electromagnetic energy and to prevent build up of solids on the interior of said coil; and
   E. control means to control flow through said line in the target area, said control means including temperature sensing means to measure differential temperature of flowable material between the upstream and downstream coil zones and to provide a variable exposure time consistent with pre-established sterilization needs of the particular flowable material being treated and to maintain the temperature below boiling.

2. The device as set forth in claim 1 wherein said coil is of a configuration such that, as seen in elevation, a substantial surface is flattened and said flattened surface is generally perpendicular to the energy path of said guide means.

3. The device as set forth in claim 1 wherein filter means are provided downstream of said target area, said filter means comprising a disposable member.

4. The device as set forth in claim 3 wherein said disposable member comprises a container having an inlet and an outlet and septum means separating the container into an upstream and a downstream chamber, said inlet means extending into said upstream chamber and a plurality of openings in said septum between said upstream chamber and said downstream chamber, a bag means in said upstream chamber, said bag having a mouth and said mouth being open to said inlet means and said bag comprising trap means to trap solids in said upstream chamber and said trap means including an outer wall of coarse netting, and a membrane captivating a mixture of porous material in the downstream chamber and constraining flow between the openings of said septum and said outlet means to passage through the membrane and porous material captivated therein to filter the same on flow through the downstream chamber.

5. The device as set forth in claim 4 wherein said inlet and outlet means of said disposable member include pressure reducing seal means assembled and non-leaking self-closure means for sealing the same when disassembled.

* * * * *